(12) United States Patent  (10) Patent No.: US 7,820,847 B2
Zeiller et al.  (45) Date of Patent: *Oct. 26, 2010

(54) BUTENOIC ACID DERIVATIVES, PROCESSES FOR THE PREPARATION THEREOF, PHARMACEUTICAL COMPOSITIONS COMPRISING THEM AND USE FOR THE TREATMENT OF DYSLIPIDAEMIA, ATHEROSCLEROSIS AND DIABETES

(75) Inventors: Jean-Jacques Zeiller, Lyons (FR); Hervé Dumas, Vaulx-Milieu (FR); Valérie Guyard-Dangremont, Saint Maurice de Gourdans (FR); Isabelle Berard, Villard les Dombes (FR); Francis Contard, Lyons (FR); Daniel Guerrier, Saint-Genis-Laval (FR); Gérard Ferrand, Lyons (FR); Yves Bonhomme, Charbonnières les Bains (FR)

(73) Assignee: Merck Patent GmbH, Darmstadt (DE)

( * ) Notice: Subject to any disclaimer, the term of this patent is extended or adjusted under 35 U.S.C. 154(b) by 1073 days.

This patent is subject to a terminal disclaimer.

(21) Appl. No.: 10/566,995

(22) PCT Filed: Jul. 14, 2004

(86) PCT No.: PCT/EP2004/007776
§ 371 (c)(1),
(2), (4) Date: Feb. 2, 2006

(87) PCT Pub. No.: WO2005/014521
PCT Pub. Date: Feb. 17, 2005

(65) Prior Publication Data
US 2006/0178434 A1 Aug. 10, 2006

(30) Foreign Application Priority Data
Aug. 4, 2003 (FR) .................................. 03 09610

(51) Int. Cl.
C07C 69/76 (2006.01)
C07C 59/00 (2006.01)
(52) U.S. Cl. ........................................ 560/81; 562/470
(58) Field of Classification Search ................. None
See application file for complete search history.

(56) References Cited
U.S. PATENT DOCUMENTS
7,465,752 B2 * 12/2008 Zeiller et al. ................. 514/443

FOREIGN PATENT DOCUMENTS
JP 52 070021 A 6/1977
JP 2001 261612 A 9/2001

OTHER PUBLICATIONS

Doyle et al, Tetrahedron Letters, 2002, 43, pp. 5929-5931.*

He et al, Journal of the American Chemical Society, Enantioselective Synthesis of a Novel Trans Double Bond Ceramide Analogue via Catalytic Asymmetric Dihydroxylation of an Enyne. The Role of the Trans Double Bond of Ceramide in the Fusion of Semiliki Forest Virus with Target Membranes, 1999, 121(16), pp. 3897-3903.*

Davies et al, Tetrahedron Letters, Regiochemistry of Molybdenum-catalyzed O-H Insertions of Vinylcarbenoids, 2000, 41, pp. 4851-4854.*

Bergmann et al, Journal of Organic Chemistry, Note on Preparation of Cyclohexen-1-aldehyde, 1958, 23, pp. 1553-1554.*

Landais et al, Synlett, Electronic Versus Steric Effects in 5-endo-trig-like Electrophilic Cyclization, 1995, (11) pp. 1191-1193.*

Database CA 'Online! Chemical Abstracts Service, Columbus, Ohio, US; Katsuda, Yoshio et al: "Insecticides" XP002274456 retrieved from STN Database accession No. 88:46409 abstract.

Database CA 'Online! Chemical Abstracts Service, Columbus, Ohio, US: Supniewski, J. et al: "p-(Diethylamino) EthoxyiPhenyl-P-Tolyl-P-Fluorophenylethanol" XP002274457, Retrieved from STN Database accession No. 59:41367 abstract.

Lin Li He: "Enantioselective Synthesis of a Novel Trans Double Bond Ceramide Analogue Via Catalytic Asymmetric Dihydroxylation of an Enyne" J.A.C.S., No. 121, 1999, pp. 3897-3903, XP002274453.

Mariko Aso: "Successive Michael Reaction-Sigmatropic Rearrangement of Polyquinones With Silyl Ketene Acetals" J.O.C., vol. 54, No. 23, 1989, pp. 5597-5603, XP002274454.

Database CA 'Online: Chemical Abstracts Service, Columbus, Ohio, US; Savard Jacques: "Reactions of Ketene Acetals-14. The Use of Simple Mixed Vinylketene Acetals in the Annulation of Quinones" XP002274458 Database accession No. 1985:131682 abstract & Tetrahedron, vol. 40, No. 18, 1984, pp. 3455-3464.

Doyle M P et al: "Chiral Catalyst Enhancement of Diastereocontrol for O@?H Insertion Reactions of Styryl-and Phenyldiazoacetate Esters of Pantolactone" Tetrahedron Letters, Elsevier Science Publishers, Amsterdam, NL, vol. 43, No. 34, Aug. 19, 2002, pp. 5929-5931, XP004373202; ISSN: 0040-4039.

(Continued)

Primary Examiner—Paul A Zucker
(74) Attorney, Agent, or Firm—Millen, White, Zelano, Branigan, P.C.

(57) ABSTRACT

The present invention relates to butenoic acid derivatives of the formula I:

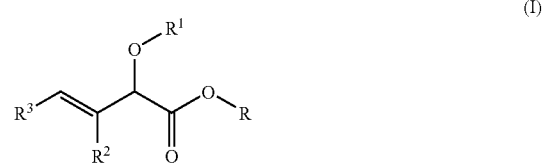

in which R, $R^1$, $R^2$ and $R^3$ are as defined in the description, and also to processes for the preparation thereof, to pharmaceutical compositions comprising them and to their use for the treatment of dyslipidaemia, atherosclerosis and diabetes.

6 Claims, No Drawings

OTHER PUBLICATIONS

Davies H M L et al: "Regiochemistry of Molybdenum-Catalyzed O-H Insertions of Vinylcarbenoids" Tetrahedron Letters, Elsevier Science Publishers, Amsterdam, NL, vol. 41, No. 25, Jun. 2000, pp. 4851-4854, XP004205669; ISSN: 0040-4039.

Y. Landais: A Stereospecific Access to Allylic Systems Using Rhodium (II)-Vinyl Carbenoid Insertion Into Si-H, O-H and N-H Bonds: J. Org. Chem., No. 62, 1997, pp. 1630-1641, XP002274455.

Database Crossfire Beilstein 'Online! Beilstein Institut Zur Förderung Der Chemischen Wissenschaften, Frankfurt Am Main, DE; Jarosz Slawomir: XP002274459; Database accession No. 3898752 abstract & Tetrahedron, vol. 38, No. 10, 1982, pp. 1447-1452.

Database Crossfire Beilstein 'Online! Beilstein Institut Zur Förderung Der Chemischen Wissenschaften, Frankfurt Am Main, DE; Guss: XP002274460; Database accession No. 439330 abstract & J.A.C.S., No. 71, 1949.

Patent Abstracts of Japan vol. 2000, No. 26, Jul. 1, 2002.

* cited by examiner

BUTENOIC ACID DERIVATIVES, PROCESSES FOR THE PREPARATION THEREOF, PHARMACEUTICAL COMPOSITIONS COMPRISING THEM AND USE FOR THE TREATMENT OF DYSLIPIDAEMIA, ATHEROSCLEROSIS AND DIABETES

The present invention relates to unsaturated carboxylic acid derivatives that can be used in the treatment of dyslipidaemia, atherosclerosis and diabetes, to pharmaceutical compositions comprising them, and to processes for the preparation of these compounds.

The invention also relates to the use of these compounds for the preparation of medicaments for the treatment of dyslipidaemia, atherosclerosis and diabetes.

In most countries, cardiovascular disease remains one of the major diseases and the main cause of death. About one third of men develop a major cardiovascular disease before the age of 60, with women showing a lower risk (ratio of 1 to 10). With advancing years (after the age of 65, women become just as vulnerable to cardiovascular diseases as men), this disease increases even more in scale. Vascular diseases, such as coronary disease, strokes, restenosis and peripheral vascular disease remain the prime cause of death and handicap worldwide.

Whereas the diet and lifestyle can accelerate the development of cardiovascular diseases, a genetic predisposition leading to dyslipidaemia is a significant factor in cardiovascular accidents and death.

The development of atherosclerosis appears to be linked mainly to dyslipidaemia, which means abnormal levels of lipoproteins in the blood plasma. This dysfunction is particularly evident in coronary disease, diabetes and obesity.

The concept intended to explain the development of atherosclerosis was mainly focused on the metabolism of cholesterol and on the metabolism of triglycerides.

However, since the studies of Randle et al. (Lancet, 1963, 785-789), a novel concept has been proposed: a glucose-fatty acid cycle or Randle cycle, which describes the regulation of the equilibrium between the metabolism of lipids in terms of triglycerides and cholesterol, and the oxygenation of glucose. Following this concept, the inventors have developed a novel programme, the aim of which is to find novel compounds acting simultaneously on lipid metabolism and glucose metabolism.

Fibrates are well-known therapeutic agents with a mechanism of action via the "Peroxisome Proliferator Activated Receptors". These receptors are the main regulators of lipid metabolism in the liver (PPARα isoform). In the last 10 years, thiazolidinediones have been described as powerful hypoglycaemiant agents in man and animals. It has been reported that thiazolidinediones are powerful selective activators of another isoform of PPARs: PPARγ (Lehmann et al., J. Biol. Chem., (1995), 270, 12953-12956).

The inventors have discovered a novel class of compounds that are powerful activators of the PPARα and PPARγ isoforms. As a result of this activity, these compounds have a substantial hypolipidaemiant and hypoglycaemiant effect.

More specifically, the invention relates to butenoic acid-derived compounds of the formula I:

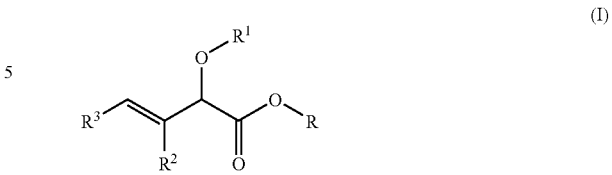

in which
R$^1$ represents a (C$_8$-C$_{18}$)aryl group, which is optionally substituted and/or optionally fused to a saturated or unsaturated, monocyclic or polycyclic 5- to 8-membered nucleus optionally containing one or more hetero atoms chosen from O, N and S, the said nucleus itself being optionally substituted; an optionally substituted, saturated, unsaturated or aromatic 5- to 8-membered monocyclic heterocyclic group containing one or more hetero atoms chosen from O, N and S; an optionally substituted C$_2$-C$_{10}$ alkenyl group; a C$_1$-C$_{10}$ alkyl group;
R$^2$ and R$^3$ independently represent a hydrogen atom; an optionally substituted (C$_6$-C$_{18}$)aryl; or alternatively R$^2$ and R$^3$ together represent a C$_3$-C$_6$ alkylene chain; and
R represents a hydrogen atom; a C$_1$-C$_{10}$ alkyl group; a (C$_6$-C$_{18}$)aryl(C$_1$-C$_{10}$)alkyl group;
and the salts thereof with acids or bases, it being understood that the following compounds are excluded from the protection:

when R$^3$=phenyl; R=ethyl; R$^1$=ethyl or phenyl; and R$^2$=H.

The acids that can be used to form the salts of the compounds of the formula I are mineral or organic acids. The resulting salts are, for example, the hydrochlorides, hydrobromides, sulfates, hydrogen sulfates, dihydrogen phosphates, citrates, maleates, fumarates, 2-naphthalenesulfonates and para-toluenesulfonates.

The bases that can be used to form the salts of the compounds of the formula I are mineral or organic bases. The resulting salts are, for example, the salts formed with metals and especially alkali metals, alkaline-earth metals and transition metals (such as sodium, potassium, calcium, magnesium or aluminium), or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The invention especially covers the pharmaceutically acceptable salts, but also the salts that allow a suitable separation or crystallisation of the compounds of the formula I, such as the salts obtained with chiral amines.

The invention also covers the optically active forms, stereoisomers, enantiomers, racemates and diastereoisomers of the compounds of the formula I, and also mixtures of these forms in all proportions.

The invention also includes the hydrate or solvate derivatives of the compounds of the formula I. The term "solvate derivatives" means the products of addition of one or more moles of inert solvent to the compounds of the formula I, which are formed on account of their mutual force of attraction. The solvate derivatives are, for example, the monohydrates, dihydrates, trihydrates, etc., or alternatively the alcoholates.

The invention thus includes all the derivatives of the compounds of the formula I that are usable and acceptable in the pharmaceutical field, for instance the salts, but also the "prodrugs" of these compounds.

The term "prodrug" denotes, for example, the compounds of the formula I that have been modified, especially with alkyl or acyl groups, sugars or oligopeptides, these being groups that are rapidly released in the body to restitute the active principles according to the present invention.

The "prodrugs" also include the derivatives of the compounds of the present invention in the form of biodegradable polymers, such as those described, for example, in *Int. J. Pharm.*, 115, 61-67, (1995).

The present invention also relates to mixtures of compounds of the general formula I as defined above, and especially mixtures of two optically active forms, for example two diastereoisomers, in all proportions, for example 1:1, 1:2, 1:3, 1:4, 1:5, 1:10, 1:100 or 1:1000.

Thus, the invention includes the compounds of the formula I, and also the pharmaceutically acceptable derivatives, salts, solvate derivatives thereof and stereoisomers thereof, including mixtures thereof in all proportions.

According to the invention, the term "aryl group" means a monocyclic or polycyclic carbocyclic aromatic group preferably containing from 6 to 18 carbon atoms. Aryl groups that may be mentioned include phenyl, naphthyl, anthryl and phenanthryl groups.

The term "alkyl" means a linear or branched hydrocarbon-based chain containing from 1 to 10 carbon atoms and better still from 1 to 6 carbon atoms, for example from 1 to 4 carbon atoms.

Examples of alkyl radicals are methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

The heterocyclic groups are monocyclic or polycyclic groups comprising hetero atoms generally chosen from O, S and N, optionally in oxidised form (in the case of S and N).

Preferably, at least one of the monocycles constituting the heterocycle contains from 1 to 4 endocyclic hetero atoms and better still from 1 to 3 hetero atoms.

According to the invention, the polycyclic heterocyclic nucleus consists of one or more monocycles, each of which is 5- to 8-membered.

Examples of 5- to 8-membered monocyclic aromatic heterocyclic groups are heteroaryls, such as pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Preferred heteroaryls that may be mentioned include pyridyl, pyrimidinyl, triazolyl, thiadiazolyl, oxazolyl, thiazolyl and thienyl nuclei.

The saturated or unsaturated heterocyclic groups are heterocyclic groups bearing no unsaturation, or comprising one or more unsaturations derived from the aromatic heterocyclic groups defined above, respectively.

The term "$C_2$-$C_{10}$ alkenyl group" means an aliphatic hydrocarbon-based group comprising one or more unsaturations of ethylenic type, preferably 1 to 3 ethylenic unsaturations. Preferred examples of such $C_2$-$C_{10}$ alkenyl groups are especially vinyl groups and $CH_2$=CH—$CH_2$—CH— groups.

When $R^2$ and $R^3$ together represent a $C_3$-$C_6$ alkylene chain, it is preferable for $R^2$, $R^3$ and the carbons to which they are attached to form a cyclopentene or a cyclohexene.

The aryl and heterocyclic groups and nuclei are optionally substituted by one or more of the following radicals:

trifluoromethyl; a halogen atom; a monocyclic, bicyclic or tricyclic aromatic heterocyclic group comprising one or more hetero atoms chosen from O, N and S; and optionally substituted by one or more radicals T as defined below; a group Het-CO— in which Het represents an aromatic heterocyclic group as defined above optionally substituted by one or more radicals T; a $C_1$-$C_6$ alkylenediyl chain; a $C_1$-$C_6$ alkylenedioxy chain; nitro; cyano; ($C_1$-$C_{10}$)alkyl; ($C_1$-$C_{10}$)alkylcarbonyl; ($C_1$-$C_{10}$)alkoxycarbonyl-A- in which A represents ($C_1$-$C_6$) alkylene, ($C_2$-$C_6$)alkenylene or a bond; ($C_3$-$C_{10}$)cycloalkyl; trifluoromethoxy; di($C_1$-$C_{10}$)alkylamino; ($C_1$-$C_{10}$)alkoxy ($C_1$-$C_{10}$)alkyl; ($C_1$-$C_{10}$)alkoxy; ($C_6$-$C_{18}$)aryl optionally substituted by one or more radicals T; ($C_6$-$C_{18}$)aryl($C_1$-$C_{10}$) alkoxy-(CO)$_n$— in which n is 0 or 1 and aryl is optionally substituted by one or more radicals T; ($C_6$-$C_{18}$)aryloxy (CO)$_n$— in which n is 0 or 1 and in which aryl is optionally substituted by one or more radicals T; ($C_6$-$C_{18}$)arylthio in which aryl is optionally substituted by one or more radicals T; ($C_6$-$C_{18}$)aryloxy($C_1$-$C_{10}$)alkyl(CO)$_n$— in which n is 0 or 1 and in which aryl is optionally substituted by one or more radicals T; a saturated or unsaturated, monocyclic 5- to 8-membered heterocycle containing one or more hetero atoms chosen from O, N and S, optionally substituted by one or more radicals T; ($C_6$-$C_{18}$)arylcarbonyl optionally substituted by one or more radicals T; ($C_6$-$C_{18}$)arylcarbonyl-B— (CO)$_n$— in which n is 0 or 1; B represents ($C_1$-$C_6$)alkylene or ($C_2$-$C_6$)alkenylene and aryl is optionally substituted by one or more radicals T; ($C_6$-$C_{18}$)aryl-C—(CO)$_n$— in which n is 0 or 1, C represents ($C_1$-$C_6$)alkylene or ($C_2$-$C_6$)alkenylene and aryl is optionally substituted by one or more radicals T; ($C_6$-$C_{18}$)aryl fused to a saturated or unsaturated heterocycle as defined above, optionally substituted by one or more radicals T; ($C_2$-$C_{10}$)alkynyl; T is chosen from a halogen atom; ($C_6$-$C_{18}$)aryl; ($C_1$-$C_6$)alkyl; ($C_1$-$C_6$)alkoxy; nitro; carboxyl; ($C_1$-$C_6$)alkoxycarboxyl; and T can represent oxo in the case where it substitutes a saturated or unsaturated heterocycle; or T represents ($C_1$-$C_6$)alkoxycarbonyl($C_1$-$C_6$)alkyl; or ($C_1$-$C_6$) alkylcarbonyl(($C_1$-$C_6$)alkyl)$_n$— in which n is 0 or 1.

The term "halogen atom" means a chlorine, bromine, iodine or fluorine atom. The monocyclic, bicyclic or tricyclic aromatic heterocyclic groups preferably comprise one or more hetero atoms generally chosen from O, S and N, optionally in oxidised form (in the case of S and N). Preferably, at least one of the monocycles constituting the heterocycle contains from 1 to 4 endocyclic hetero atoms and better still from 1 to 3 hetero atoms.

Preferably, the heterocycle consists of one or more monocycles, each of which is 5- to 8-membered.

Examples of 5- to 8-membered monocyclic heteroaryls are especially pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Examples of bicyclic heteroaryls in which each monocycles is 5- to 8-membered are chosen from indolizine, indole, isoindole, benzofuran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazine (such as pyrazolo-1,3,4-triazine), pyrazolopyrimidine and pteridine.

Preferred heteroaryls that may be mentioned include quinolyl, pyridyl, benzothiazolyl and triazolyl.

The tricyclic heteroaryls in which each monocycle is 5- to 8-membered are chosen, for example, from acridine, phenazine and carbazole.

The term "alkylenediyl chain" means a divalent radical of linear or branched aliphatic hydrocarbon-based type derived from the alkyl groups defined above by stripping out a hydrogen atom. Preferred examples of alkylenediyl chains are chains —$(CH_2)_k$— in which k represents an integer chosen from 2, 3, 4, 5 and 6 and >$C(CH_3)_2$ and —$CH_2$—$C(CH_3)_2$—$CH_2$— chains. The alkylenedioxy chains denote —O-Alk-O— chains in which Alk represents linear or branched alkylene, it being understood that alkylene is as defined above for alkylenediyl. Preferred meanings of —-Alk-O— are, for example, —O—$C(CH_3)_2$—O— or —O—$CH_2$—$CH_2$—O—.

The term "alkenylene" defines an unsaturated alkylene chain containing one or more ethylenic unsaturations, preferably one to three ethylenic unsaturations. Examples of alkylene chains are —CH=CH— or —CH=CH—CH=CH—.

Examples of $C_3$-$C_{10}$ cycloalkyl groups are especially cyclopropyl, cyclobutyl, cyclopentyl, cyclohexyl, cycloheptyl, cyclooctyl or cyclodecyl groups.

Saturated or unsaturated, monocyclic 5- to 8-membered heterocycles are saturated, or unsaturated, derivatives of aromatic heterocycles.

Mention may be made more particularly of morpholine, piperidine, thiazolidine, oxazolidine, tetrahydrothienyl, tetrahydrofuryl, pyrrolidine, isoxazolidine, imidazolidine or pyrazolidine.

The term "alkynyl" means an aliphatic hydrocarbon-based group containing one or more unsaturations of acetylenic type. Preferred examples are —C≡C—.

Another preferred group of compounds of the invention consists of the compounds of the formula I in which $R^1$ represents a ($C_6$-$C_{10}$)aryl group, preferably phenyl, which is optionally substituted and/or fused to a carbocyclic or heterocyclic monocyclic 5- to 8-membered nucleus containing from 0 to 4 hetero atoms chosen from O, N and S, which is itself optionally substituted; an optionally substituted $C_2$-$C_{10}$ alkenyl group; a hydrogen atom; $R^2$ and $R^3$ independently represent a hydrogen atom; ($C_6$-$C_{10}$)aryl, preferably optionally substituted phenyl; or $R^2$ and $R^3$ together represent a $C_5$-$C_8$ alkylene chain; and R represents a hydrogen atom; a $C_1$-$C_{10}$ alkyl group; a ($C_6$-$C_{10}$)aryl($C_1$-$C_{10}$)alkyl group.

Another preferred subgroup of compounds of the invention consists of the compounds of the formula I in which, when $R^1$ represents a substituted ($C_6$-$C_{10}$)aryl, the aryl nucleus is substituted by one or more of the following radicals: trifluoromethyl; a halogen atom; a monocyclic, bicyclic or tricyclic aromatic heterocyclic group comprising one or more hetero atoms chosen from O, N and S; and optionally substituted by one or more radicals T as defined below; a group Het-CO— in which Het represents an aromatic heterocyclic group as defined above, optionally substituted by one or more radicals T; a $C_1$-$C_6$ alkylenediyl chain; a $C_1$-$C_6$ alkylenedioxy chain; nitro; cyano; ($C_1$-$C_{10}$)alkyl; ($C_1$-$C_{10}$)alkylcarbonyl; ($C_1$-$C_{10}$)alkoxycarbonyl-A- in which A represents ($C_1$-$C_6$)alkylene, ($C_2$-$C_6$)alkenylene or a bond; ($C_3$-$C_{10}$)cycloalkyl; trifluoromethoxy; di($C_1$-$C_{10}$)alkylamino; ($C_1$-$C_{10}$)alkoxy($C_1$-$C_{10}$)alkyl; ($C_1$-$C_{10}$)alkoxy; ($C_6$-$C_{18}$)aryl optionally substituted by one or more radicals T; ($C_6$-$C_{18}$)aryl($C_1$-$C_{10}$)alkoxy-$(CO)_n$— in which n is 0 or 1 and aryl is optionally substituted by one or more radicals T; ($C_6$-$C_{18}$)aryloxy$(CO)_n$— in which n is 0 or 1 and in which aryl is optionally substituted by one or more radicals T; ($C_6$-$C_{18}$)arylthio in which aryl is optionally substituted by one or more radicals T; ($C_6$-$C_{18}$)aryloxy($C_1$-$C_{10}$)alkyl$(CO)_n$— in which n is 0 or 1 and in which aryl is optionally substituted by one or more radicals T; a saturated or unsaturated, monocyclic 5- to 8-membered heterocycle comprising one or more hetero atoms chosen from O, N and S, optionally substituted by one or more radicals T; ($C_6$-$C_{18}$)arylcarbonyl optionally substituted by one or more radicals T; ($C_8$-$C_{18}$)arylcarbonyl-B—$(CO)_n$— in which n is 0 or 1; B represents ($C_1$-$C_6$)alkylene or ($C_2$-$C_6$)alkenylene and aryl is optionally substituted by one or more radicals T; ($C_6$-$C_{18}$)aryl-C—$(CO)_n$— in which n is 0 or 1, C represents ($C_1$-$C_6$)alkylene or ($C_2$-$C_6$)alkenylene and aryl is optionally substituted by one or more radicals T; ($C_6$-$C_{18}$)aryl fused to a saturated or unsaturated heterocycle as defined above, optionally substituted by one or more radicals T; ($C_2$-$C_{10}$)alkynyl; T is chosen from a halogen atom; ($C_6$-$C_{18}$)aryl; ($C_1$-$C_6$)alkyl; ($C_1$-$C_6$)alkoxy; nitro; carboxyl; ($C_1$-$C_6$)alkoxycarboxyl; and T can represent oxo in the case where it substitutes a saturated or unsaturated heterocycle; or alternatively T represents ($C_1$-$C_6$)alkoxycarbonyl($C_1$-$C_6$)alkyl; or ($C_1$-$C_6$)alkylcarbonyl(($C_1$-$C_6$)alkyl)$_n$— in which n is 0 or 1.

Another group of preferred compounds consists of the compounds of the formula I for which, when $R^1$ represents aryl, $R^1$ is phenyl.

Another group of preferred compounds consists of the compounds for which $R^1$ represents ($C_1$-$C_{10}$)alkyl, preferably ($C_1$-$C_3$)alkyl, and $R^2$ and $R^3$ represent, independently of each other, H or optionally substituted ($C_6$-$C_{18}$) aryl.

Another group of preferred compounds consists of the compounds for which $R^2$ is H and $R^3$ represents unsubstituted aryl, preferably unsubstituted phenyl.

Another group of preferred compounds consists of the compounds for which, when R represents ($C_1$-$C_{10}$)alkylaryl, preferably benzyl, $R^1$ and $R^3$ represent unsubstituted aryl, preferably phenyl.

A first even more preferred group of compounds of the invention consists of the compounds of the formula I in which $R^1$ represents an unsubstituted aryl group, $R^2$ represents H, $R^3$ represents unsubstituted aryl and R is H.

A second even more preferred group of compounds of the invention consists of the compounds of the formula I in which $R^1$ represents unsubstituted aryl, $R^2$=H, $R^3$ is unsubstituted aryl and R=alkyl.

A third even more preferred group of compounds of the invention consists of the compounds of the formula I in which $R^1$=unsubstituted aryl, $R^2$=H. $R^3$=unsubstituted aryl and R=alkylaryl.

A fourth even more preferred group of compounds of the invention consists of the compounds of the formula I in which $R^1$=substituted aryl, $R^2$=H, $R^3$=unsubstituted aryl and R=H.

A fifth even more preferred group of compounds of the invention consists of the compounds of the formula I in which R1 represents substituted aryl, R2=H, R3 is unsubstituted aryl and R=alkyl.

A sixth even more preferred group of compounds of the invention consists of the compounds of the formula I in which $R^1$ represents substituted aryl, $R^2$=H. $R^3$ is unsubstituted aryl and R=alkylaryl.

A seventh even more preferred group of compounds of the invention consists of the compounds of the formula I in which $R^1$ represents alkyl, $R^2$=H, $R^3$ is unsubstituted aryl and R=H.

An eighth even more preferred group of compounds of the invention consists of the compounds of the formula I in which $R^1$ represents alkyl, $R^2$=H, $R^3$ is unsubstituted aryl and R=alkyl.

A ninth even more preferred group of compounds of the invention consists of the compounds of the formula I in which $R^1$ represents alkyl, $R^2$=H, $R^3$ is unsubstituted aryl and R=alkylaryl.

The compounds that are more particularly preferred are chosen from:
methyl(R,S)-2-methoxy-4-phenylbut-3-enoate
(R,S)-2-methoxy-4-phenylbut-3-enoic acid
methyl(R,S)-2-propoxy-4-phenylbut-3-enoate
(R,S)-2-propoxy-4-phenylbut-3-enoic acid
benzyl (R,S)-2-phenoxy-4-phenylbut-3-enoate
methyl(R,S)-2-trifluoromethylphenoxy-4-phenylbut-3-enoate
(R,S)-2-phenoxy-4-phenylbut-3-enoic acid
(R,S)-2-trifluoromethylphenoxy-4-phenylbut-3-enoic acid (Z and E forms).

The compounds of the invention can be prepared by reaction of a compound of the formula II

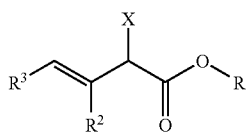
(II)

in which $R^2$, $R^3$ and R are as defined above for formula I and X represents —OH or a halogen atom, such as chlorine, with an alcohol of the formula $R^1$—OH.

This reaction is preferably performed in a polar aprotic solvent, such as a linear or cyclic ether, for example diethyl ether, di-tert-butyl ether, diisopropyl ether or dimethoxyethane, or alternatively, such as dioxane or tetrahydrofuran, tetrahydrofuran and dimethoxyethane being preferred.

According to one preferred embodiment of the invention, the molar ratio of the compound of the formula II to the alcohol $R^1$—OH ranges between 1 and 1.5, an approximately stoichiometric ratio of between 1 and 1.3 and preferably between 1 and 1.1 being desirable.

In order to facilitate the reaction, it is desirable to add to the medium a coupling agent, such as a lower alkyl (i.e. $C_1$-$C_6$ alkyl) diazodicarboxylate, for example ethyl diazodicarboxylate.

When it is present in the reaction medium, the coupling agent is incorporated into the medium in a proportion of from 1 to 5 equivalents and better still in a proportion of from 1 to 3 equivalents, for example in a proportion of from 1 to 2 molar equivalents relative to the initial amount of compound of the formula II.

Preferably, it is also recommended to introduce a phosphine into the reaction medium, such as triphenylphosphine. In this case, the molar ratio of triphenylphosphine to the compound of the formula II is preferably maintained between 1 and 5, for example between 1 and 3 and especially between 1 and 2.

When X represents —OH, the reaction temperature generally ranges between −15° C. and 50° C., it being understood that temperatures of between −15° C. and 10° C. are desirable in the presence of a coupling agent.

When X represents a halogen atom, the compound of the formula II is represented by formula $II_{Hal}$ below:

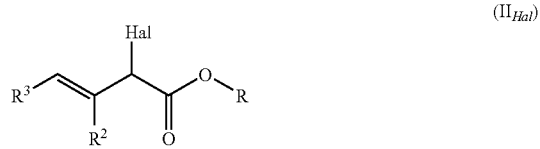
($II_{Hal}$)

in which R, $R^2$ and $R^3$ are as defined above and Hal represents a halogen atom.

With a compound of the formula $II_{Hal}$, as defined above, a base is introduced into the reaction medium, preferably a mineral base chosen from sodium hydroxide, potassium hydroxide, sodium hydrogen carbonate, potassium hydrogen carbonate, sodium carbonate and potassium carbonate. Usually, the molar ratio of the base to the compound of the formula II ranges between 1 and 5 and better still between 1 and 3.

When X represents a halogen atom, the reaction temperature generally ranges between 10° C. and 120° C.; for example between 60° C. and 100° C. and better still between 70° C. and 90° C.

When X represents halogen, for example chlorine, the compounds of the formula I of the invention can be obtained according to the following reaction scheme, in which R, $R^1$, $R^2$ and $R^3$ are as defined above:

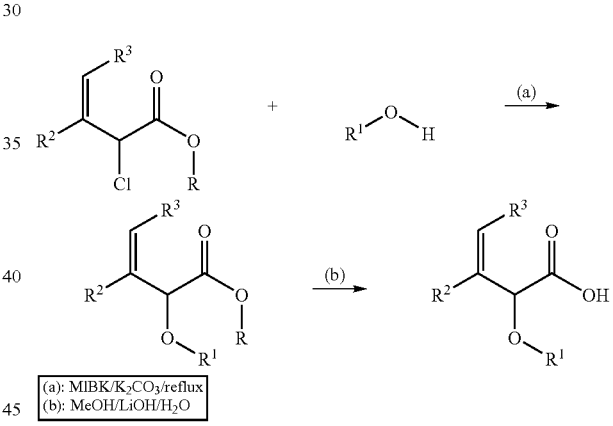

(a): MIBK/$K_2CO_3$/reflux
(b): MeOH/LiOH/$H_2O$

The compounds of the formula I can be prepared by selective reduction of the oxo function alpha to the function —COOR in the compound of the formula III below:

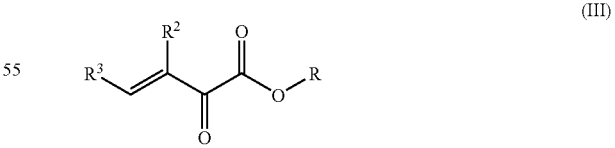
(III)

in which R, $R^2$ and $R^3$ are as defined above, via the action of a suitable hydride, followed by alkylation of the hydroxyl function formed.

Examples of suitable hydrides are especially sodium borohydride, lithium borohydride, tributylammonium borohydride, lithium triethylborohydride and sodium cyanoborohydride, sodium borohydride being preferred.

The reaction is preferably performed in a solvent, such as a lower alkanol, such as methanol or propanol, at a temperature of between −15° C. and 20° C. and preferably between −10° C. and +10° C.

For this reaction, the molar ratio of the hydride to the compound of the formula III ranges between 0.1 and 10 equivalents. When the hydride is NaBH$_4$, 0.2 to 0.5 equivalent of NaBH$_4$ is sufficient.

The alkylation of the intermediate compound, obtained via the action of the hydride

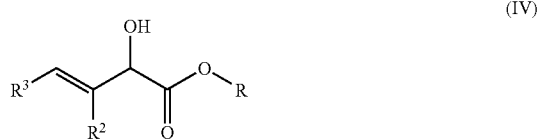

(IV)

in which $R^2$, $R^3$ and R are as defined above for formula I, can be performed in a manner that is conventional per se.

One way of performing the process consists simply in reacting the intermediate compound of the formula IV with the appropriate alkyl halide of the formula $R^1$—Y in which Y is a halogen atom, preferably iodine, in the presence of silver oxide, Ag$_2$O.

For this reaction, a large excess of the alkylating agent of the formula $R^1$—Y, for example from 5 to 200 equivalents and better still between 100 and 150 equivalents relative to the initial amount of compound of the formula IV, will advantageously be used.

As regards the amount of Ag$_2$O, it is desirable for it to range between 2 and 12 equivalents, for example between 4 and 10 equivalents.

The compounds of the formula I can also be prepared via the action of an alcohol of the formula $R^1$—OH on a compound of the formula V

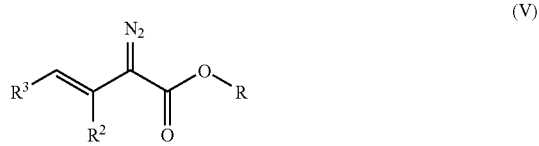

(V)

in which $R^2$, $R^3$ and R are as defined above, in the presence of a rhodium II complex, such as rhodium II tetraacetate of the formula Rh$_2$(OAc)$_4$.

This reaction is preferably performed in a polar aprotic solvent, such as an optionally chlorinated aromatic hydrocarbon, for example benzene, toluene, xylene or a chlorobenzene, benzene being preferred.

A molar ratio of the alcohol $R^1$—OH to the compound of the formula V ranging between 1 and 10, for example between 1 and 5 and better still between 2 and 4, is preferably used for this reaction.

It is desirable for the rhodium complex to be present in a proportion of from $10^{-3}$ to $10^{-1}$ equivalent relative to the compound of the formula V, a ratio of the rhodium complex to the compound of the formula V of between 0.01 and 0.10 and better still between 0.01 and 0.05 being preferred.

The reaction temperature is usually between 50° C. and 120° C., for example between 60° C. and 100° C.

The compounds of the formula I in which R represents H can be obtained by saponification of the corresponding compounds of the formula I in which R represents C$_1$-C$_{10}$ alkyl. The saponification can be performed via the action of a base, such as a mineral base chosen from LiOH, KOH, NaOH, NaHCO$_3$, KHCO$_3$, Na$_2$CO$_3$ and K$_2$CO$_3$. The molar amount of base to be used generally ranges from 1 to 20 equivalents and preferably from 1 to 12 equivalents depending on the strength of the selected base.

More particularly, in the case of LiOH, it is preferred to employ from 8 to 12 equivalents of base relative to the amount of ester of the formula I present in the reaction medium.

The reaction is preferably performed in a solvent of polar protic type and more preferably in a mixture of lower (C$_1$-C$_4$) alkanol and water, such as a mixture of ethanol and water or methanol and water.

The reaction temperature advantageously ranges between 35° C. and 120° C. and better still between 40° C. and 100° C.

The compounds of the formula I in which $R^1$ represents aryl substituted by a monocyclic, bicyclic or tricyclic aromatic heterocyclic group comprising one or more hetero atoms chosen from O, N and S, and optionally substituted by one or more radicals T as defined above; or alternatively $R^1$ represents an aryl group optionally substituted by one or more radicals T, can be prepared by reaction of the corresponding compound of the formula I in which $R^1$ represents aryl substituted by a halogen atom, such as chlorine, bromine or iodine, via the action of a compound of the formula VI:

(VI)

in which G represents a monocyclic, bicyclic or tricyclic aromatic heterocyclic group comprising one or more hetero atoms chosen from O, N and S, and optionally substituted by one or more radicals T as defined above when $R^1$, in the final compound, represents aryl substituted by such a heterocyclic group, or alternatively G represents aryl optionally substituted by one or more radicals T when, in the final compound, $R^1$ represents aryl substituted by an aryl group, which Is itself optionally substituted by one or more radicals T.

Advantageously, from 1.5 to 5 equivalents and preferably from 1.5 to 3 equivalents of the compound of the formula VI are employed relative to the amount of compound of the formula I present in the reaction medium.

This reaction is preferably performed in a polar aprotic solvent in the presence of a palladium(0) complex and a base.

A linear or cyclic ether, such as those defined above is more particularly suitable as solvent. Dimethoxyethane is preferred.

The base that will be used is any of the mineral bases mentioned above and advantageously Na$_2$CO$_3$. For example, from 1.5 to 5 equivalents and preferably from 1.5 to 3 equivalents of base, relative to the amount of compound of the formula I, can be introduced into the reaction medium.

According to one preferred embodiment, the amounts of base and of compound of the formula VI are equivalent. The amount of palladium(0) complex used is catalytic. Usually, from 0.001 to 1 equivalent and preferably from 0.01 to 0.1 equivalent of the said complex is used. An example of a palladium(0) complex that can be used is tetraphenylpalladium(0).

The reaction temperature advantageously ranges between 50° C. and 120° C. and preferably between 70° C. and 90° C.

The invention also relates to pharmaceutical compositions comprising a pharmaceutically effective amount of a compound of the formula (I) as defined above in combination with one or more pharmaceutically acceptable vehicles.

In the present description, the expression "pharmaceutically effective amount" should be understood as defining the amount of an active material or of a pharmaceutical agent that will make it possible to induce the biological or medical response of an animal or human tissue or system, this biological or medical response corresponding to the response desired, for example, by a researcher or a clinician.

In addition, the expression "therapeutically effective amount" corresponds to any amount which, in comparison with a corresponding individual who has not received such amount, results in an improved treatment, curing, better prevention, or improvement of a pathological condition, a disorder or one or more side effects, or alternatively results in a reduction in the degree of advancement of a disease or pathological disorder. The expression described above also includes in its meaning amounts that are effective for improving a normal physiological function.

Thus, the pharmaceutical compositions according to the present invention can be administered orally in the form of tablets, gel capsules or granules with immediate release or controlled release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrating agent, a lubricant, a colorant or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly(vinyl ether), ethylcellulose, methylcellulose, acacia, gum tragacanth, gelatine, shellac, hydroxypropylcellulose, hydroxy-propylmethylcellulose, calcium citrate, dextrin and pectin. Examples of lubricants include magnesium stearate, talc, polyethylene glycol, silica and hardened plant oils. The colorant may be any of those permitted for used in medicaments. Examples of flavour enhancers include cocoa powder, mint in herb form, aromatic powder, mint in oil form, borneol and cinnamon powder. Obviously, the tablet or granule may be suitably coated with sugar, gelatine or the like.

An injectable form comprising the compound of the present invention as active principle is prepared, where appropriate, by mixing the said compound with a pH regulator, a buffer agent, a suspension agent, a solubiliser, a stabiliser, an isotonic agent and/or a preserving agent, and by converting the mixture into a form for intravenous, subcutaneous or intramuscular injection, according to a standard process. Where appropriate, the injectable form obtained can be freeze-dried via a standard process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilisers include castor oil solidified with polyoxyethylene, polysorbate 80, nicotinamide, polyethoxylated sorbitan monolaurate and the ethyl ester of castor oil fatty acid.

In addition, the stabiliser encompasses sodium sulfite, sodium metasulfite and ether, while the preserving agent encompasses methyl p-hydroxybenzoate, ethyl p-hydroxybenzoate, sorbic acid, phenyl, cresol and chlorocresol.

A subject of the present invention is also the use of a compound of the formula I of the invention for the preparation of a medicament for the prevention or treatment of dyslipidaemia, atherosclerosis and diabetes.

The examples that follow illustrate the invention in a non-limiting manner.

In the proton nuclear magnetic resonance data (300 MHz NMR), the following abbreviations have been used: s for singlet, d for doublet, t for triplet, q for quartet, o for octet and m for complex multiplet. The chemical shifts $\delta$ are expressed in ppm; m.p. represents the melting point.

EXAMPLES

Example 1

Process for the Preparation of methyl(R,S)-2-hydroxy-4-phenylbut-3-enoate 1.1—Preparation of methyl 2-oxo-4-phenylbut-3-enoate 2 ml of concentrated sulfuric acid are added dropwise to a suspension of 5.9 g (30 mmol) sodium 2-oxo-4-phenylbut-3-enoate (1) (Synth. Commun., (1996), 26(11), 2231) in 100 ml of methanol. The mixture is refluxed for 8 hours and stirred overnight at room temperature. A light insoluble material is filtered off and the filtrate is concentrated to half its volume and poured into 300 ml of water. The pasty solid obtained is extracted with dichloromethane and washed with aqueous 5% sodium hydrogen carbonate solution and then with water. The resulting solution is dried over sodium sulfate. The solvent is evaporated off under vacuum. The residue (4.2 g) is purified by flash chromatography ($SiO_2$, 70/30 $CH_2Cl_2$/heptane).

1.7 g (30% yield) of a bright yellow solid melting at 70-71° C. are obtained.

$^1$H NMR ($CDCl_3$, 300 MHz): 3.86 (3H, s); 7.31 (1H, d, J=16 Hz); 7.27-7.58 (5H, m); 7.80 (1H, d, J=16 Hz).

1.2—Process for the preparation of methyl (R,S)-2-hydroxy-4-phenylbut-3-enoate 0.27 g (7 mmol) of sodium borohydride is added portionwise, over about 10 minutes, to a solution of 4.2 g (22 mmol) of methyl 2-oxo-4-phenylbut-3-enoate in 150 ml of methanol, cooled to 0° C. The mixture is stirred for 10 minutes between 0° C. and +5° C. and then allowed to warm to room temperature. The resulting mixture is evaporated under vacuum at 40° C., the residue is taken up in 100 ml of water, the resulting mixture is extracted with dichloromethane and the organic extracts are dried over sodium sulfate. The solvent is evaporated off under vacuum. The residue (3.7 g) is purified by flash chromatography ($SiO_2$, 80/20 heptane/ethyl acetate).

2.2 g (52% yield) of a yellow oil are obtained.

$^1$H NMR ($CDCl_3$, 300 MHz): 3.00 (1H, OH); 3.70 (3H, s); 4.73-4.75 (1H, d, J=6 Hz); 6.11-6.17 (1H, dd, J=16 Hz, J=6 Hz); 6.67-6.73 (1H, d, J=16 Hz); 7.15-7.30 (5H, m).

Example 2

Process for the preparation of methyl(R,S)-2-methoxy-4-phenylbut-3-enoate 1.8 g (8 mmol) of freshly prepared silver oxide are added to a solution of 225 mg (1.2 mmol) of the compound obtained in Example 1 in 10 ml of methyl iodide. The mixture is stirred for 24 hours at room temperature and then diluted with 10 ml of dichloromethane. The insoluble material is filtered off and the filtrate is then evaporated under vacuum. 210 mg (85% yield) of a colourless oil are obtained.

Example 3

Process for the preparation of (R,S)-2-methoxy 4-phenylbut-3-enoic acid 42 ml (42 mmol) of aqueous 1M lithium hydroxide monohydrate solution are added to a solution of 0.87 g (4.2 mmol) of the compound obtained in Example 2 in 80 ml of methanol. The mixture is refluxed for 4 hours. After leaving to stand overnight, the mixture is evaporated under vacuum and the residue is taken up in 40 ml of water. This mixture is washed with 2×30 ml of ethyl ether and the aqueous phase is acidified with dilute hydrochloric acid. The resulting aqueous phase is extracted with ethyl ether, the organic extracts are dried over sodium sulfate and the solvent is evaporated off under vacuum. The residue (0.65 g) is purified by flash chromatography ($SiO_2$, 95/5 dichloromethane/methanol). 50 mg (6% yield) of a yellow oil are obtained.

Example 4

Process for the preparation of (R,S)-2-n-propoxy-4-phenylbut-3-enoic acid 480 mg (2 mmol) of the compound obtained in Example 3, 10 ml of ethanol, 1 ml of water and 270 mg (4 mmol) of potassium hydroxide pellets are refluxed for 4 hours. The mixture is evaporated under vacuum and the residue is taken up in 25 ml of water. This mixture is washed with ethyl ether and the aqueous phase is acidified with dilute hydrochloric acid. The resulting mixture is extracted with ethyl ether, the organic extracts are dried over sodium sulfate and the solvent is evaporated off under vacuum. The residue (310 mg) is purified by flash chromatography ($SiO_2$, 80/20 heptane/ethyl acetate). 45 mg (10% yield) of a yellowish oil are obtained.

Illustration of the Reaction Scheme of Examples 1 to 4, $R^1$=alkyl.

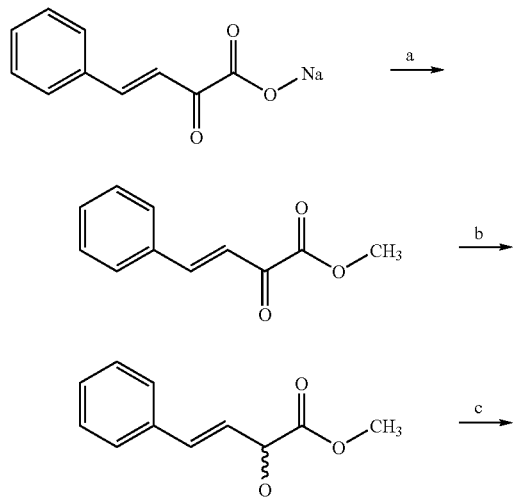

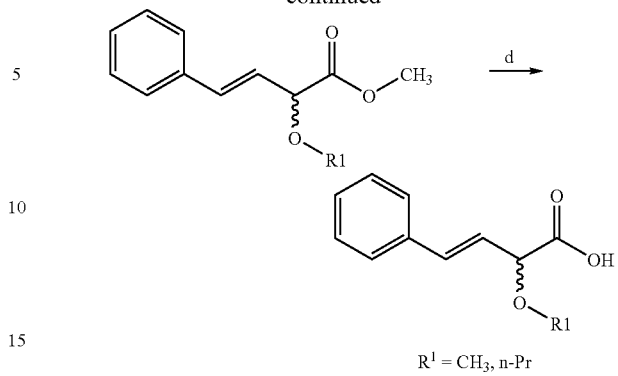

(a): MeOH/$H_2SO_4$
(b): $NaBH_4$/MeOH
(c): $Ag_2O$/R1-1
(d): $OH^-$/$H_2O$/MeOH/then $H^+$

Example 5

Process for the Preparation of methyl(R,S)-4-phenyl-2-(4-trifluoromethylphenoxy)but-3-enoate 300 mg (0.67 mmol) of dimeric rhodium acetate are added to a solution of 14.6 g of 4-trifluoromethylphenol in 150 ml of benzene. The mixture is brought to reflux and a solution of 6.2 g (30 mmol) of methyl 4-phenyl-2-diazobut-3-enoate (6) (*Tetrahedron Lett.*, (1988), 29(9), 975-978) in 60 ml of benzene is added dropwise over one hour. The mixture is allowed to cool to room temperature and the solvent is then evaporated off under vacuum. The residue is purified twice by flash chromatography. 460 mg (4.6% yield) of a yellow oil which crystallises are obtained.

Example 6

Process for the Preparation of (R,S)-4-phenyl-2-(4-trifluoro-methylphenoxy)but-3-enoic acid 12.2 ml (12.2 mmol) of aqueous 1M lithium hydroxide monohydrate solution are added to a solution of 410 mg (1.22 mmol) of the compound obtained in Example 5 in 20 ml of sodium hydroxide. The mixture is stirred for one hour at room temperature and the solvent is then evaporated off under vacuum. The residue is taken up in 20 ml of water and the solution obtained is washed with ethyl ether. The aqueous phase is acidified with dilute hydrochloric acid and extracted with ethyl ether. The organic extracts are dried over sodium sulfate and the solvent is evaporated off under vacuum. The residue is purified by preparative LC/MS. Two pure products (8) and (9) corresponding to the two Z and E forms (5.5 mg and 7.8 mg, respectively) are recovered.

Illustration of the Reaction Scheme of Examples 5 and 6. $R^1$=substituted aryl(trifluoromethylphenyl), Steps a) and b)

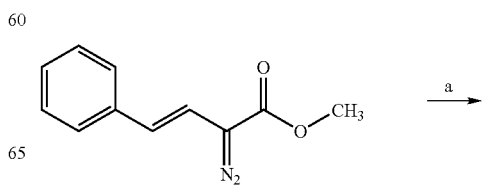

15

-continued

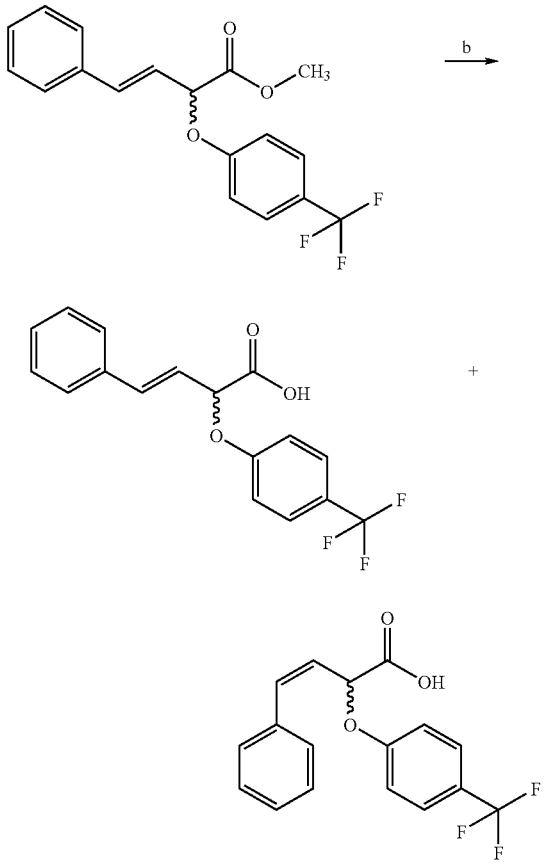

(a): p-CF$_3$PhOH/Rh$_2$(OAc)$_4$/Bz
(b): OH-/then H+

Results

The activity of the compounds of the invention leading to a hypolipidaemiant and hypoglycaemiant effect was demonstrated in vitro by performing the following tests:

The measurement of the PPAR activation was performed according to a technique described by Lehmann et al. (*J. Biol. Chem.*, 270, (1995), 12953-12956).

CV-1 cells (monkey kidney cells) are co-transfected with an expression vector for the chimeric proteins PPARα-Gal4 or PPARγ-Gal4 and with a "reporter" plasmid that allows the expression of the luciferase gene placed under the control of a promoter containing Gal4 response elements.

The cells are plated into 96-well microplates and co-transfected using a commercial reagent with the reporter plasmid (pG5-tk-pGL3) and the expression vector for the chimeric protein (PPARα-Gal4 or PPARγ-Gal4). After incubating for 4 hours, whole culture medium (comprising 10% foetal calf serum) is added to the wells. After 24 hours, the medium is removed and replaced with whole medium comprising the test products (50 μM final). The products are left in contact with the cells for 18 hours. The cells are then lysed and the luciferase activity is measured using a luminometer. A PPAR activation factor can then be calculated by means of activation of the expression of the reporter gene induced by the product (relative to the control cells that have not received any product).

16

By way of example, the compound

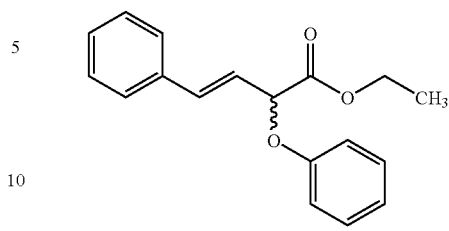

at a concentration of 50 μM, activates the chimeric protein PPARα-Gal-4 by a factor of 2.3, and the chimeric protein PPARγ-Gal4 by a factor of 6.4. In the absence of the binding domain for the PPAR α or γ ligand (vector expressing Gal4 alone), the luciferase activity measured in the presence of this product is zero.

The invention claimed is:

1. A compound of the formula I:

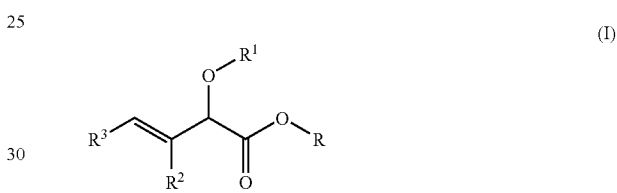

in which

R$^1$ represents a (C$_6$-C$_{10}$)aryl group, which is optionally substituted and/or fused to a carbocyclic or heterocyclic monocyclic 5- to 8-membered nucleus containing from 0 to 4 hetero atoms chosen from O, N and S, which is itself optionally substituted; or an optionally substituted C$_2$-C$_{10}$ alkenyl group;

R$^2$ is a substituted phenyl;

R$^3$ is a substituted phenyl; and

R represents a hydrogen atom; a C$_1$-C$_{10}$ alkyl group; a (C$_6$-C$_{10}$)aryl (C$_1$-C$_{10}$)alkyl group;

or a salt thereof with acids or bases, or a pharmaceutically acceptable derivative, or stereoisomer thereof, including mixtures thereof in all proportions.

2. A compound according to claim 1, wherein R$^1$ represents phenyl.

3. A compound according to claim 1, wherein R$^1$ represents (C$_1$-C$_{10}$)alkyl.

4. A compound which is:

(R,S)-2-methoxy-4-phenylbut-3-enoic acid methyl (R,S)-2-propoxy-4-phenylbut-3-enoate (R,S)-2-propoxy-4-phenylbut-3-enoic acid benzyl (R,S)-2-phenoxy-4-phenylbut-3-enoate methyl (R,S)-2-trifluoromethylphenoxy-4-phenylbut-3-enoate (R,S)-2-phenoxy-4-phenylbut-3-enoic acid (R,S)-2-trifluoromethylphenoxy-4-phenylbut-3-enoic acid (Z and E forms), or a pharmaceutically acceptable derivative, salt or stereoisomer thereof, including mixtures thereof in all proportions.

5. A compound according to claim 1, wherein $R^1$ is a phenyl which is optionally substituted and/or fused to a carbocyclic or heterocyclic monocyclic 5- to 8-membered nucleus containing from 0 to 4 hetero atoms chosen from O, N and S, which is itself optionally substituted.

6. A compound of the formula I:

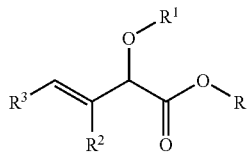

(I)

in which $R^1$ represents unsubstituted aryl, $R^2$ is a hydrogen atom or an optionally substituted ($C_6$-$C_{18}$) aryl;

$R^3$ is an unsubstituted aryl; and

R represents a benzyl;

or a salt thereof with acids or bases, or a pharmaceutically acceptable derivative, or stereoisomer thereof, including mixtures thereof in all proportions.

* * * * *